United States Patent
Hauser et al.

[19]

[11] Patent Number: 5,916,238
[45] Date of Patent: *Jun. 29, 1999

[54] IMPLANTABLE INTRAVENOUS CARDIAC STIMULATION SYSTEM WITH PULSE GENERATOR HOUSING SERVING AS OPTIONAL ADDITIONAL ELECTRODE

[75] Inventors: Robert G. Hauser, Long Lake; Roger W. Dahl, Andover; Bruce H. KenKnight, Robbinsdale, all of Minn.

[73] Assignee: Cardiac Pacemakers, Inc., St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/964,120

[22] Filed: Nov. 4, 1997

Related U.S. Application Data

[63] Continuation of application No. 08/380,538, Jan. 30, 1995, Pat. No. 5,713,926, which is a continuation of application No. 07/917,899, Jul. 24, 1992, Pat. No. 5,385,574, which is a continuation-in-part of application No. 07/514,251, Apr. 25, 1990, Pat. No. 5,133,353.

[51] Int. Cl.⁶ ...................................................... A61N 1/39
[52] U.S. Cl. ................................................................ 607/5
[58] Field of Search ........................................ 607/4, 5, 6

[56] References Cited

U.S. PATENT DOCUMENTS

| | | | |
|---|---|---|---|
| 3,614,955 | 10/1971 | Mirowski | 607/6 |
| 4,548,203 | 10/1985 | Tacker, Jr. et al. | 128/419 |
| 4,662,377 | 5/1987 | Heilman et al. | 128/419 |
| 4,727,877 | 3/1988 | Kallok | 128/419 |
| 4,817,608 | 4/1989 | Shapland et al. | 128/419 |
| 4,944,300 | 7/1990 | Saksena | 128/419 |
| 4,953,551 | 9/1990 | Mehra et al. | 128/419 |
| 5,050,601 | 9/1991 | Kupersmith et al. | 128/419 |
| 5,083,562 | 1/1992 | de Coriolis et al. | 128/419 |
| 5,107,834 | 4/1992 | Ideker et al. | 128/419 |
| 5,111,811 | 5/1992 | Smits | 128/419 |
| 5,133,353 | 7/1992 | Hauser | 128/419 |
| 5,209,229 | 5/1993 | Gilli | 128/419 |
| 5,261,400 | 11/1993 | Bardy | 607/5 |
| 5,383,908 | 1/1995 | Sweeny et al. | 607/5 |

OTHER PUBLICATIONS

Jones, D.L., et al., "Internal Cardiac Defibrillation in Man: Pronounced Improvement with Sequential Pulse Delivery to Two Different Lead Orientations", *Circulation*, vol. 73, No. 3, pp. 484–491, (Mar. 1986).

*Primary Examiner*—William E. Kamm
*Attorney, Agent, or Firm*—Schwegman, Lundberg Woessner & Kluth P.A.

[57] ABSTRACT

A pulse generator housing for enclosing and containing pulse generator defibrillation circuitry. The housing is formed entirely of electrically conductive metal defining an electrically conductive outer surface which is connected to the pulse generator circuitry for delivering defibrillating energy to the heart. The pulse generator housing is implanted in the pectoral region proximate the heart with the conductive surface facing the heart. Regions of the conductive outer surface may be electrically isolated and dedicated for separately sensing and shocking. The outer surface may be coated with platinum. Additional coiled segment electrodes may extend from the housing and be electrically connected to the conductive outer surface so as to increase the effective conductive surface area. A sensor is provided to determine whether the housing is inside or outside a body of a patient to disconnect the pulse generator housing conductive surface from the pulse generator circuitry when the unit is outside the body of a patient.

4 Claims, 9 Drawing Sheets

IMPLANTABLE INTRAVENOUS CARDIAC STIMULATION SYSTEM WITH PULSE GENERATOR HOUSING SERVING AS OPTIONAL ADDITIONAL ELECTRODE

RELATED APPLICATION

This application is a continuation of application Ser. No. 08/380,538, filed Jan. 30, 1995, now U.S. Pat. No. 5,313,926, which is a continuation of application Ser. No. 07/917,899, filed Jul. 24, 1992, now U.S. Pat. No. 5,385,574, which is a continuation-in-part of U.S. patent application Ser. No. 07/514,251, filed Apr. 25, 1990, now U.S. Pat. 5,133,353.

BACKGROUND OF THE INVENTION

This invention relates to an implantable cardiac stimulation lead and electrode system for applying electrical energy to an abnormally functioning heart and more particularly to an implantable pulse generator housing having electrically conductive walls serving as a defibrillation discharge electrode.

Electrodes implanted in the body for electrical stimulation of muscle or body organs are well known. More specifically, electrodes implanted on or about the heart have been used to reverse certain abnormal and life-threatening arrhythmias. Electrical energy is applied to the heart via the electrodes to return the heart to normal sinus rhythm.

Common abnormal cardiac arrhythmias include bradycardia (slower than normal heartbeat rhythm), ventricular tachycardia (faster than normal heartbeat rhythm), and ventricular fibrillation (sporadic and uncoordinated beating of the heart). The latter two arrhythmias generally are fatal if left untreated.

To control the heartbeat rhythm and prevent fatalities from ventricular tachycardia and fibrillation, several devices have been designed having the ability to stimulate the heart according to a sensed cardiac signal such as a sensed ECG signal. See for example U.S. Pat. No. 4,603,705 to Speicher et al. The Speicher et al. patent discloses a multiple electrode unitary intravascular cardiac catheter having a distal electrode for sensing and pacing, an intermediate electrode for sensing, pacing and cardioverting, and a proximal electrode for sensing and cardioverting. This multiple electrode catheter maintains the ability for heart rate sensing and low threshold pacing immediately following cardioversion.

There are many types of defibrillation cardioversion electrodes in the art. U.S. Pat. No. 4,825,871 to Cansell discloses a defibrillation/cardioversion shock system in which the box housing the pulse generator circuitry serves as a support for a discharge electrode. Specifically, the metal box is enclosed by a plastics material and a metal plate is attached to the metal box and electrically connected therewith. Charges collected by the metal plate are transmitted to the metal box, which serves as a collector. The metal box itself is not used as an electrode in the Cansell system.

The need therefore exists for implantable cardiac stimulation lead system capable of performing standard pacing, such as anti-bradycardia pacing, anti-tachycardia pacing, low-energy cardioversion, and high-energy defibrillation.

SUMMARY OF THE INVENTION

It is a primary object of this invention to provide an implantable cardiac stimulation lead system having pacemaking, cardioversion and higher energy defibrillation capabilities.

It is an additional object of this invention to provide an implantable cardiac stimulation lead system having pacemaking, cardioversion and defibrillation capabilities via a selectable defibrillation electrode configuration.

It is yet a further object of this invention to provide an implantable cardiac stimulation lead system utilizing a relatively small number of implantable parts.

It is still another object of the present invention to provide an implantable pulse generator housing made entirely or partially but in a selective manner, of electrically conductive material, serving as a defibrillation electrode.

It is yet a further object of the invention to provide an electrically conductive portion of an implantable pulse generator housing which, together with electrical discharge surfaces extending therefrom, serve as an electrode.

It is still another object of the present invention to reduce the size of the pulse generator housing by eliminating one terminal on the housing.

Briefly, the implantable cardiac stimulation lead system of the present invention comprises a transvenous endocardial or epicardial lead having a plurality of electrodes. Typically, the lead electrodes are capable of sensing and performing standard anti-bradycardia pacing, anti-tachycardia pacing, cardioversion and defibrillation. The transvenous lead is connected to a pulse generator having full-function pacing capabilities as well as cardioversion and defibrillation capabilities. The housing of the pulse generator (together with, as desired, electrical discharge surfaces extending therefrom) is conductive and is connected to the pulse generator circuitry so that it may selectively serve as a discharge electrode. The outer surface of the pulse generator could be of a special configuration to facilitate its discharge capabilities. Typically, the pulse generator is implanted in the pectoral or abdominal region of the body proximate the heart. A programmable switch or other type of circuitry is provided to select the electrode configuration which may include or exclude the pulse generator housing electrode. As a result, different electrode configurations can be obtained for specific types of cardiac stimulations.

In a first embodiment, the electrode surface of the pulse generator housing comprises a portion of the conductive wall of the housing.

In a second embodiment, the electrode surface comprises conductive mesh attached to the pulse generator housing.

In a third embodiment, the pulse generator housing is a metal housing, all or selective ones of the surfaces of which, together with, as desired, electrical discharge surfaces extending therefrom, are conductive.

In accordance with a fourth embodiment, the other surface of the conductive pulse generator housing is platinum.

The fifth embodiment relates to dedicating isolated conductive surface regions from one another, such isolated regions may serve for separately sensing, pacing and shocking.

In accordance with the sixth embodiment, an insulative mask is disposed over a conductive surface of the pulse generator housing.

In a seventh embodiment, a sensing switch is used to determine when the pulse generator is implanted and when it is outside the body of the patient.

The above objects and advantages of the present invention can be further understood when reference is made to the following description, taken in conjunction with the accompanying drawings.

DETAILED DESCRIPTION OF THE DRAWINGS

Figure 1:
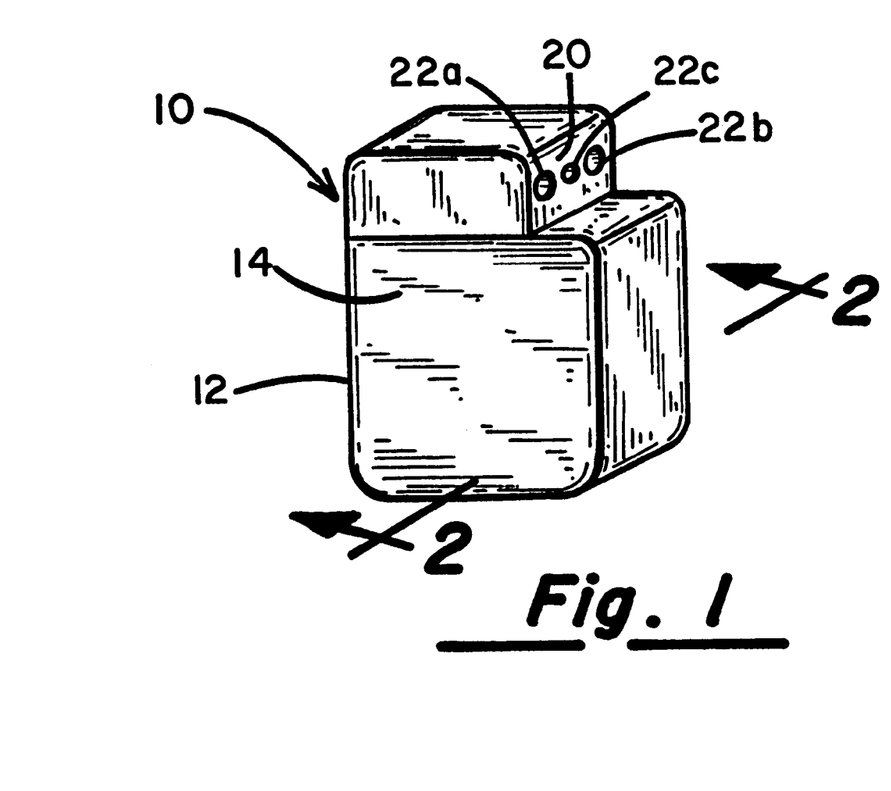
FIG. 1 is a perspective view illustrating the pulse generator housing serving as a cardiac electrode in accordance with a first embodiment of the present invention.
Figure 2:
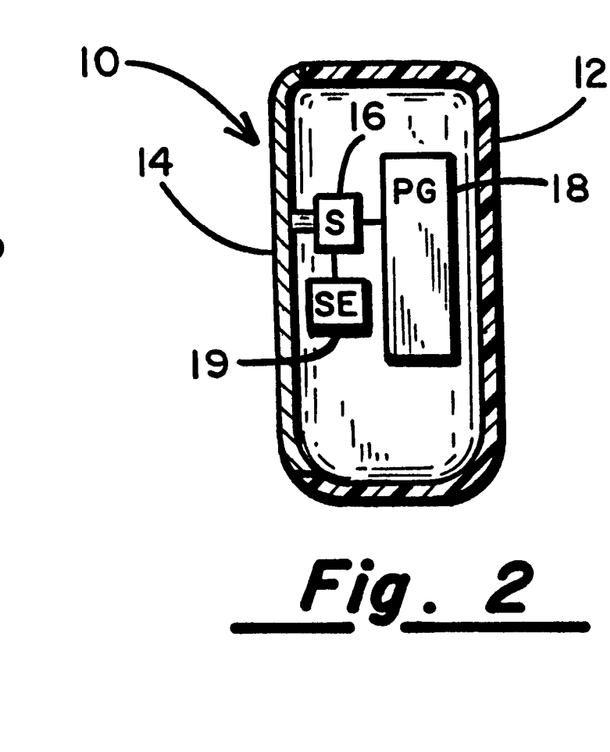
FIG. 2 is a cross-sectional view taken through line 2—2 of FIG. 1.

Referring to FIGS. 1 and 2, the pulse generator housing of the present invention is generally shown at 10. Typically, housing 10 is of a rectangular box shape having four side walls, a top wall, and a bottom wall. In one embodiment, at least one of the side walls is highly conductive. To this end, housing 10 includes side wall 12 having an outer discharge surface 14 formed of highly electrically conductive material. The conductive surface 14 is connected to the pulse generator circuitry 18 via a programmable switch 16. The pulse generator circuitry 18 is insulated from the outer discharge surface and electrically connected to electrode lead plug receptacle assembly 20.

As previously mentioned, the number of side walls of housing 10 having conductive discharged surfaces may vary. However, it is envisioned that as many as (or more than) four side walls may be made electrically conductive.

Figure 3:
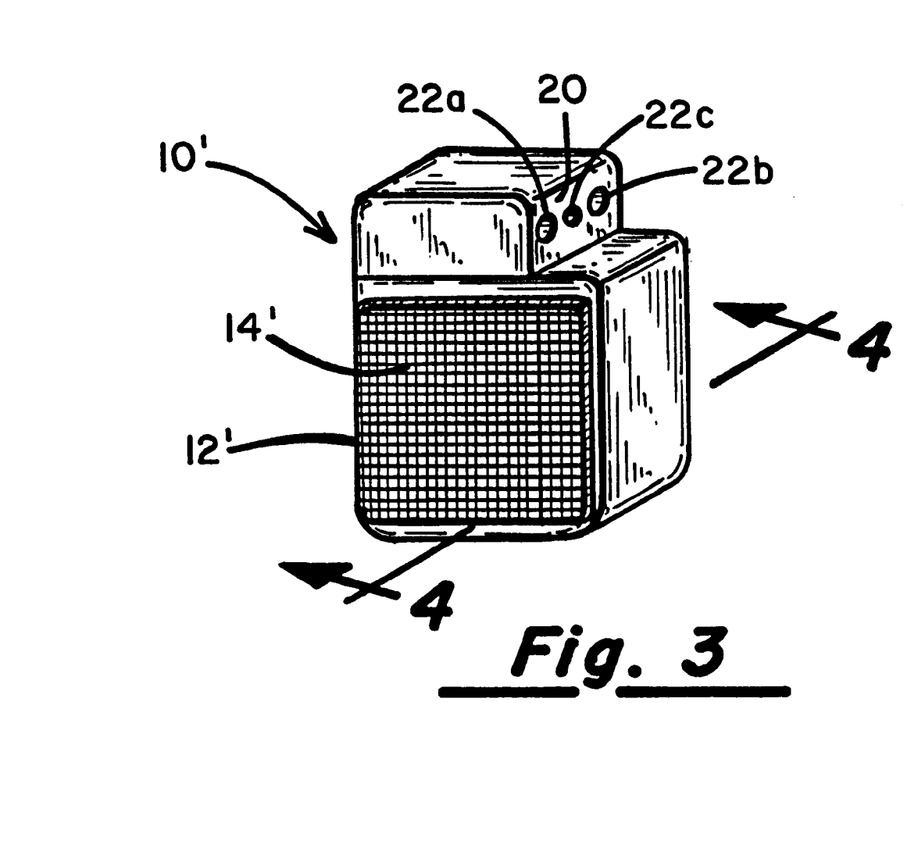
FIG. 3 is a perspective view illustrating the pulse generator housing having conductive mesh on a face thereof for serving as a cardiac electrode in accordance with the second embodiment of the present invention.
Figure 4:
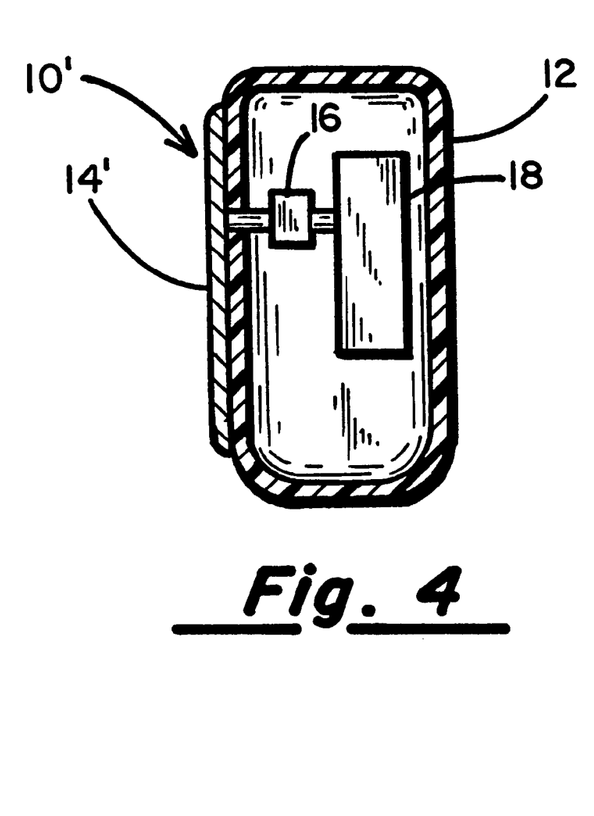
FIG. 4 is a cross-sectional view taken through line 4—4 of FIG. 3.

Referring now to FIGS. 3 and 4, a pulse generator housing of a second embodiment is illustrated at 10'. Housing 10' is similar to housing 10 of FIGS. 1 and 2 except the side wall 12' includes a conductive mesh surface 14'. It is to be understood that, hereinafter, the term "mesh" includes that as illustrated as well as any other high surface area conductive materials including microtextured materials. As shown in FIG. 4, conductive mesh surface 14' is electrically connected via switch 16 to pulse generator circuitry 18 contained within housing 10'. In addition a separate conductive patch (not shown) could be added and connected to the bottom of the pulse generator housing to increase the conductive surface area. This patch could attach by a snap or other similar means to the housing.

The removable pulse generator patch electrode may take several forms. One form may be a subcutaneous array comprised of a helical coil which encircles the pulse generator housing, and plugs into a terminal or the housing. Another form may be an array of parallel or radiating conductive fingers which are funneled subcutaneously proximate the pulse generator housing. A clamp may be provided to connect the patch electrode to the pulse generator housing.

Figure 12:
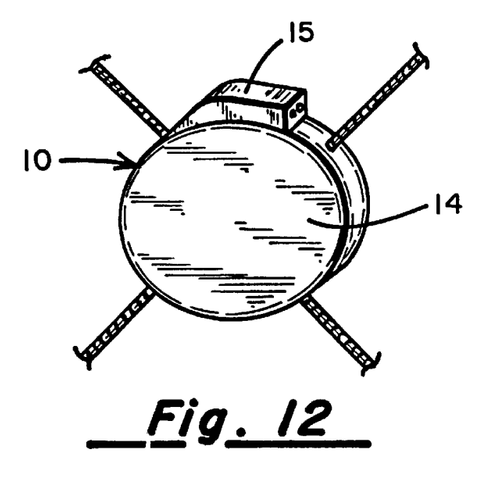
FIG. 12 is a perspective view of the pulse generator housing with extending discharge surfaces according to a seventh embodiment.
Figure 13:
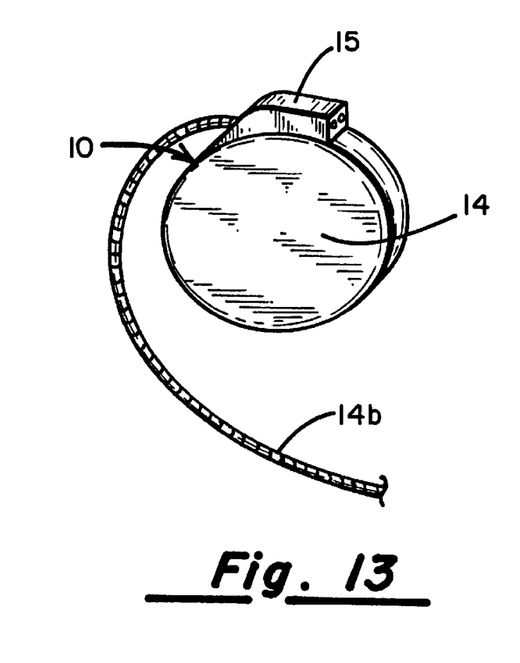
FIG. 13 is a perspective view of the pulse generator housing with extending discharge surfaces according to an eighth embodiment.
Figure 14:
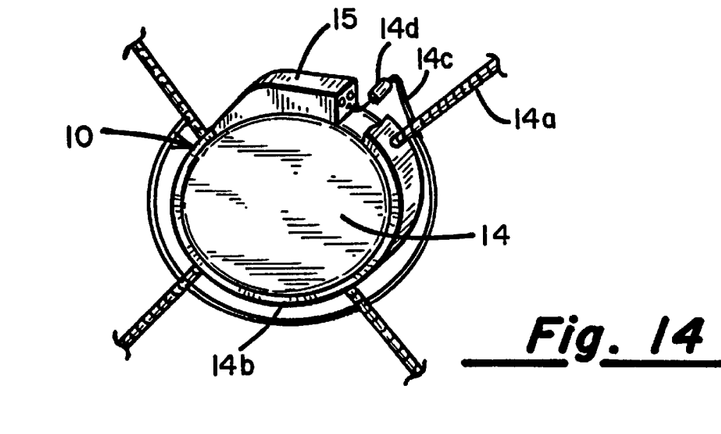
FIG. 14 is a perspective view of the pulse generator housing with extending discharge surfaces according to a ninth embodiment.

In another embodiment, additional electrical discharge surfaces may be connected to the pulse generator housing 10. Thus, as illustrated in FIG. 12, a plurality of coiled segment electrodes 14a, tunnelled subcutaneously in the patient, may be connected so as to protrude from and form a contiguous electrical discharge surface with the pulse generator housing 10. This additional discharge surface area increases the efficiency of the combined coil segments/ housing electrode by decreasing the impedance and increasing the effective electrode surface area. This combination has particular application to counter-shock treatment of tachyarrhythmias. An alternative embodiment is illustrated in FIG. 13, in which a coiled loop 14b connected to a header 15 and disposed outside the SQ pocket serves as the additional discharge surface area. In yet another embodiment, illustrated in FIG. 14, a to membrane 14b, e.g. a silicone rubber layer, is attached to the side of housing 10. Coiled segment electrodes 14a are joined to and protrude from membrane 14b, membrane 14b both supporting and providing structural orientation for coiled segment electrodes 14a. Lead 14c electrically connects all electrodes 14a, and is electrically connected via plug 14d to the plug receptacle of pulse generator 10.

Figure 15:
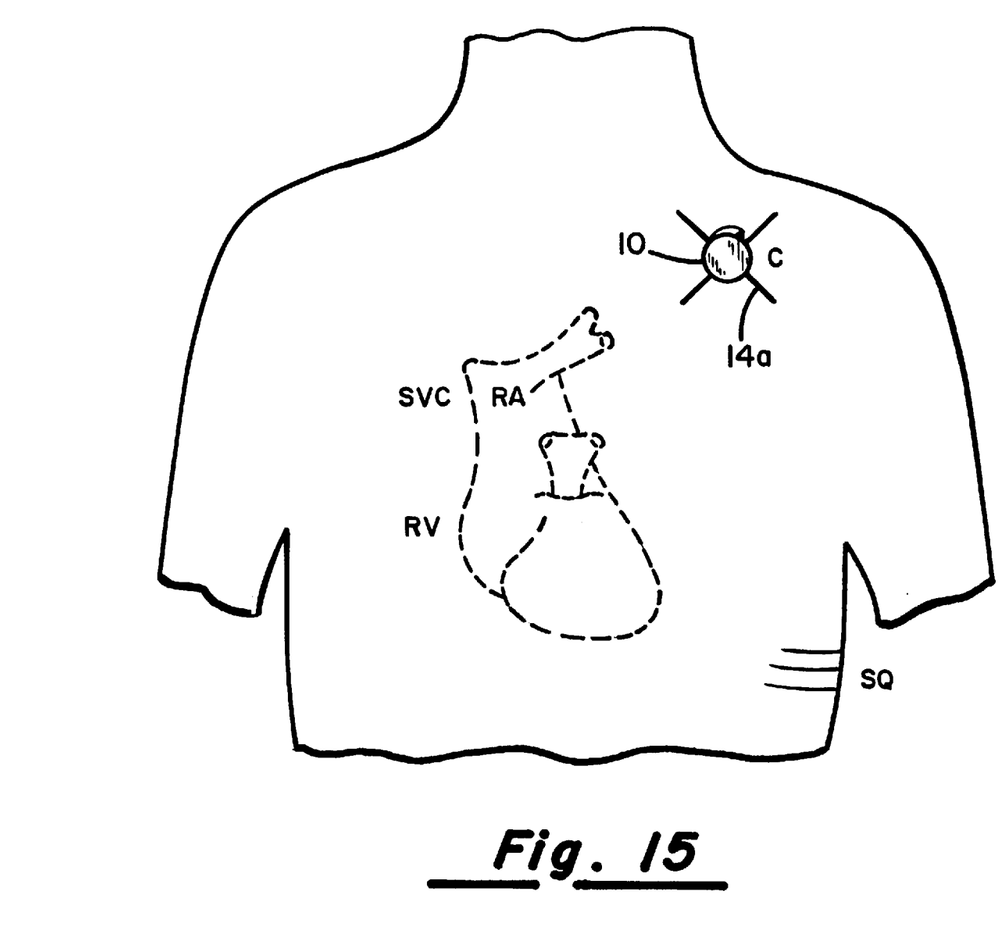
FIG. 15 is a front view of a patient illustrating a discharge configuration including the pulse generator according to the seventh embodiment.

FIG. 15 shows a discharge configuration now possible through use of an electrically conductive pulse generator housing of the present invention. In this configuration the pulse generator housing 10 is implanted so as to function as a pectoral electrode (position C). Discharge paths are possible from an electrode at position RV to electrodes at positions SVC and C, as well as from electrodes at RV and SVC to electrodes at C and SQ. Further, this configuration may be used to terminate atrial arrhythmias with shocks given from SVC to C (or, alternatively, from SVC to SQ, or to C and SQ). Similarly, a pectoral electrode (housing 10) at C may be used for effecting atrial defibrillation by using a discharge path between an active electrode at RA and the housing 10 at position C.

The plug receptacle assembly 20 comprises a positive port 22a and a negative port 22b. This allows connection of implanted electrodes to the pulse generator circuitry, so that one electrode may serve as anode and one electrode may serve as a cathode. If desired, either electrode could be used in combination with the electrically conductive housing.

A sensor 19 is provided to determine whether the housing 10 is outside the body of a patient or inside the body. The purpose of the sensor 19 is to prevent a shock from be delivered while the housing is outside the body and perhaps held in the hand of a physician prior to implant. The sensor 19 may be a thermal sensor to detect when the housing is at body temperature, indicative of being inside the body. The sensor 19 controls the switch 16 to permit shocking via the pulse generator housing. When the temperature is other than body temperature, the sensor 19 controls the switch 16 so as to prevent discharge via the pulse generator housing by prohibiting connection to the pulse generator circuitry.

Alternatively, the sensor may be embodied as a signal detector to detect some signal for a period of time before shocking. As a result, a shock may not be delivered when the unit is outside the body and not sensing signals from the body.

Pulse generator circuitry 18 has full-function pacing capabilities including pacing for bradycardia and tachycardia both to inhibit an intrinsic beat or to adapt the rate to a higher or lower rate. In addition, circuitry 18 has cardioversion and defibrillation capabilities and includes cardiac detection circuitry capable of distinguishing when the heart is in normal sinus rhythm, should be paced, or requires higher energy cardioversion, or defibrillation. The switch 16 is selectively activated to include or exclude the conductive surface(s) of the pulse generator housing 10 during the discharge sequence.

Figure 5:
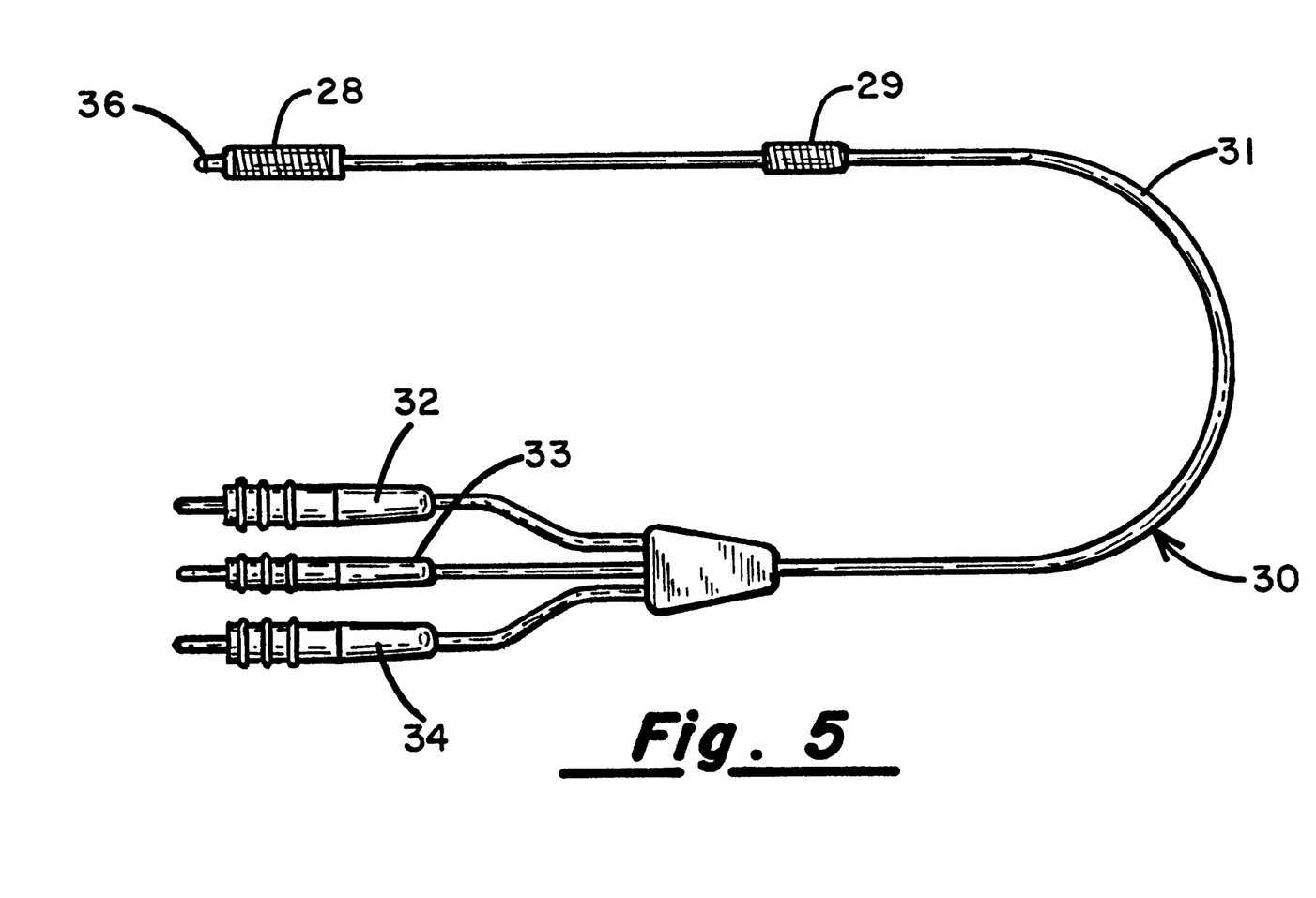
FIG. 5 is a side view of a transvenous electrode and lead used in conjunction with the p1lse generator illustrated in FIG. 1 or FIG. 3.

Pulse generator housing 10 or 10' is typically used in conjunction with other cardiac electrodes implanted on or about a human heart. One such lead is illustrated in FIG. 5. Lead 30 is provided having a catheter portion 31 supporting electrode 28 on the distal end as well as electrode 29 on a proximate end of catheter portion 31. Lead 30 includes plug connectors 32–34 at its proximal end. In addition, a sensing tip electrode 36 may be provided at the distal tip of catheter portion 31 for sensing cardiac activity. Electrodes 28 and 29 could also have sensing capabilities.

Figure 6:
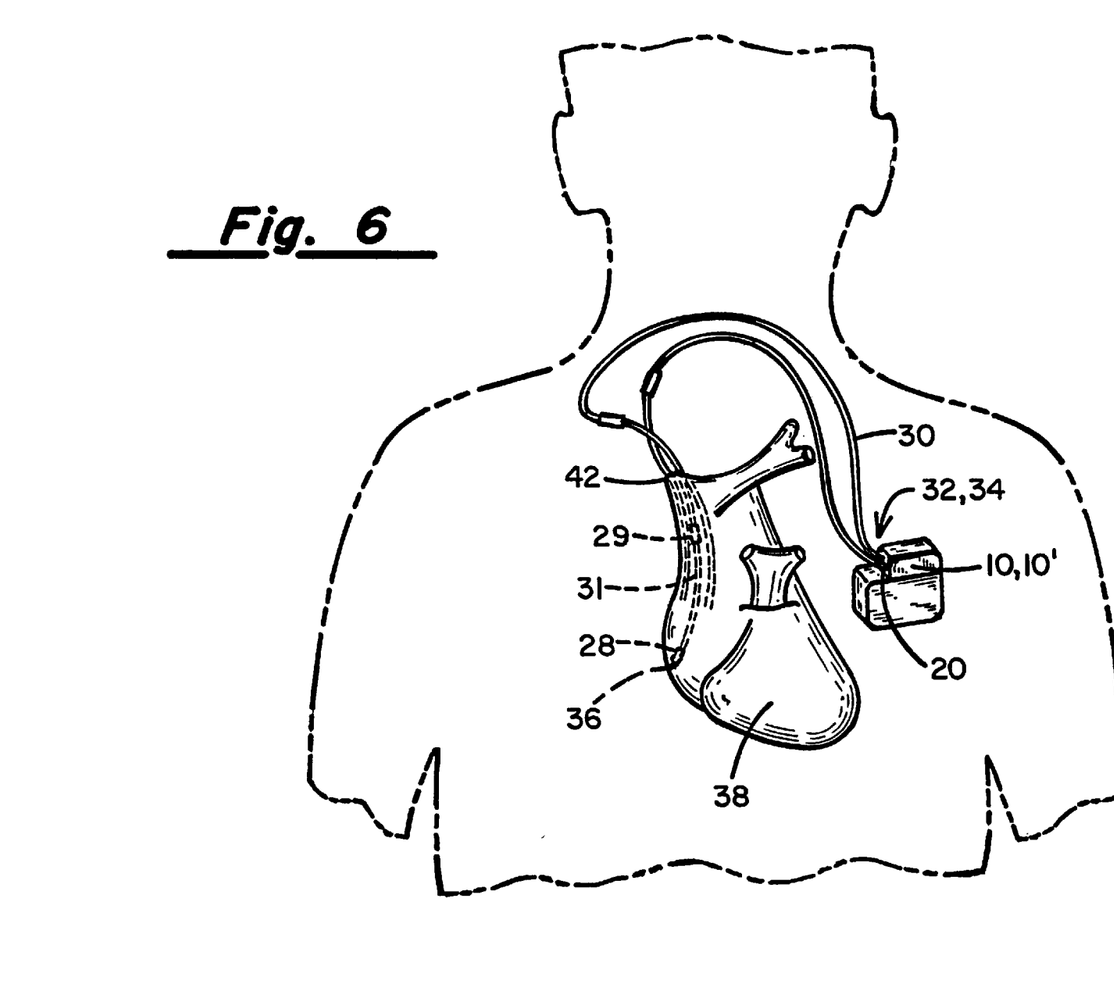
FIG. 6 is a diagram illustrating the placement of the pulse generator housing adjacent the heart and connected to the implanted transvenous electrode and lead.

Referring to FIG. 6, in operation, lead 30 is implanted transvenously in the human heart 38 with electrode 28 in the right ventricle 40 and electrode 29 proximate the right atrium or the superior vena cava 42. Alternatively, a single catheter electrode may be used for placing the electrode in the right ventricle. Pulse generator housing 10 or 10' is implanted in the pectoral region proximate but not in contact with the heart, just under the skin. Alternatively, the housing 10 or 10' could be implanted in the abdominal region. Plug connectors 32–34 are inserted into the appropriate ports 22a, 22b or 22c (not shown) of the receptacle assembly 20. In this implantation position, the electrode surface of the pulse generator housing may be used in a two electrode or three electrode configuration, and may replace one of the intravascular catheter electrodes.

Figure 17:
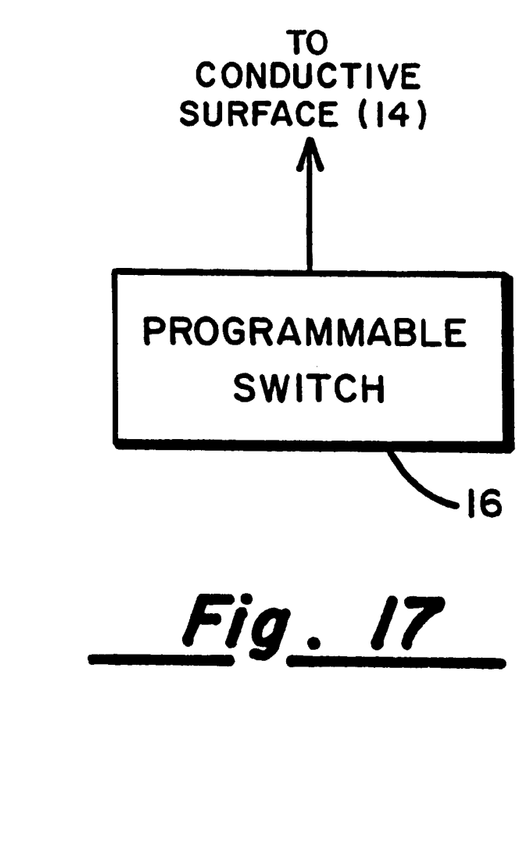
FIG. 17 is a block diagram showing the programmabel switch.

Referring additionally to FIG. 17, when an arrhythmia is sensed where it is appropriate for an electrical pulse to be delivered to the heart 38, the programmable switch 16 determines which electrodes are energized under control of circuitry 18. The switch is programmed so that it can select any combination of three electrodes, such as, for example, any combination of the right ventricular (RV) electrode 28, pulse generator electrode surface 14 and superior vena cava (SVC) electrode 42. The superior vena cava electrode 42 may be replaced by a subcutaneous electrode. The RV electrode is connected to terminal 22a and the SVC or subcutaneous electrode is connected to terminal 22b. The pulse generator conductive surface would be electrically connected in common with the SVC or subcutaneous electrode. The switch 16 may be programmed to discharge the RV electrode against the SVC (or subcutaneous) electrode and/or the pulse generator electrode surface(s).

In another possible configuration, if the heart activity is slower or faster (bradycardia or tachycardia) than normal, the switch 16 is triggered so that the pulse generator circuitry 18 selects only electrode 28 to discharge to the pulse generator housing. On the other hand, if the sensed activity is indicative of rapid ventricular tachycardia or fibrillation requiring higher energy stimulation, the switch 16 is triggered so that the pulse generator circuitry 18 selects both distal and proximal electrodes 28 and 29, respectively, as well as the electrode discharge surface 14 to discharge energy from the conductive wall(s) of housing 10 or 10' for delivering defibrillation electrical energy to the heart 38.

Also, prior to applying a high energy defibrillating shock to the heart, a lower energy cardioverting shock can be applied between electrodes 28 and 29 against the conductive wall(s) of the pulse generator housing 10 or 10'. Thereafter, if the heart does not revert back to normal sinus rhythm, the higher energy defibrillation pulse is applied across the same electrodes.

In yet another alternate form, the programmable switch 16 may be programmed to select one of the electrodes 28 and 29, and the conductive electrode surface(s) of the pulse generator housing 10 or 10'. In this way, the electrode discharge surface 14 of the pulse generator housing 10 or 10' will be discharged against only one of the electrodes 28 or 29. Further, the choice between the electrodes 28 and 29 may be based on certain cardiac conditions.

Figure 7:
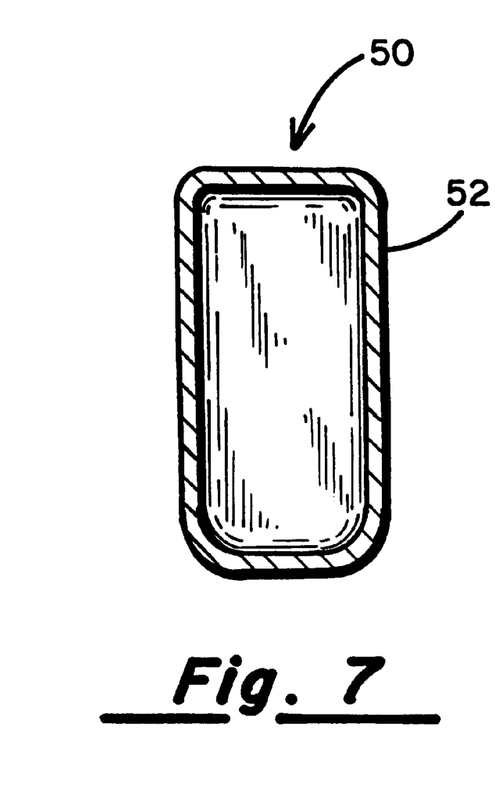
FIG. 7 is a cross-sectional view of the pulse generator housing according to a third embodiment of the present invention.
Figure 8:
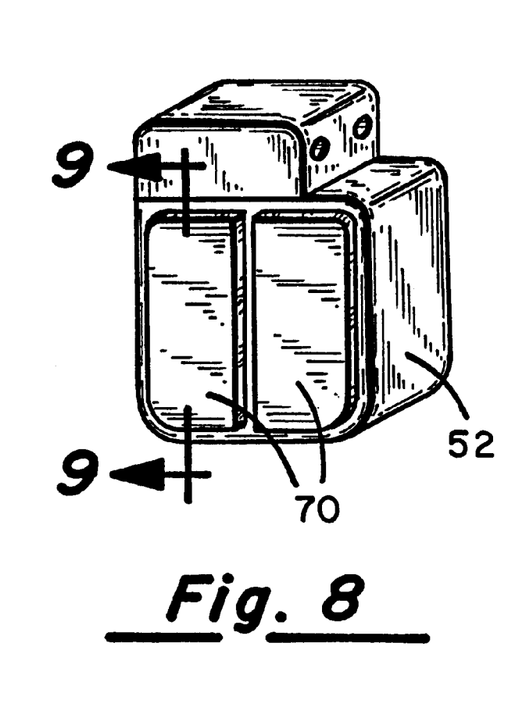
FIG. 8 is a perspective view of the pulse generator housing according to a fourth embodiment.
Figure 9:
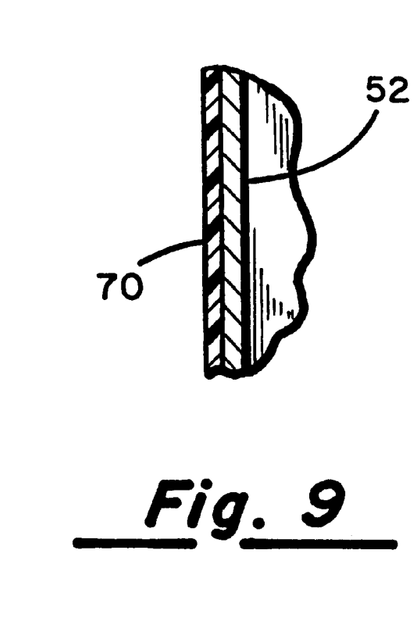
FIG. 9 is a cross-sectional view taken through line 9—9 of FIG. 8.

FIG. 7 illustrates a pulse generator housing 50 according to a third embodiment. The housing 50 is comprised of a titanium body 52. The internal pulse generator circuitry 18 and programmable switch 16 are connected to the body 52 as described in conjunction with FIG. 2. The entire outer surface of the body 52 may be conductive or selective surface portions may be made insulative. Specifically, as shown in FIGS. 8 and 9, an insulative ceramic material 70 may be sputtered (e.g. high energy plasma deposition) onto the conductive outer surface of the body 52. This is useful to create a conductive surface which has a controlled current density, in much the same manner as recently developed defibrillation cardioversion patch electrodes. See, for example, commonly assigned U.S. Pat. No. 5,063,932. The insulative material may take the form of a mask or in various patterns known to control current density across a conductive surface. The insulative material may also take the form of silicone rubber.

Figure 10:
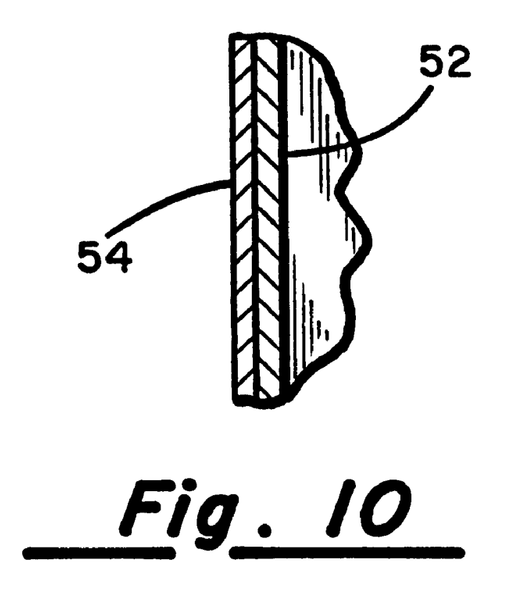
FIG. 10 is a cross-sectional view of a portion of the pulse generators housing illustrating a fifth embodiment.

FIG. 10 illustrates a modification to the embodiment of FIG. 7 in which the outer surfaces of the body 52 of the pulse generator housing 50 are coated with platinum 54, a metal which does not anodize, thus maintaining performance of the housing walls 52 as an anode. The platinum surface may be created by sputtering or high energy plasma deposition and further may be made a microporous surface to minimize kinetic losses (reduce interface impedance).

Figure 11:
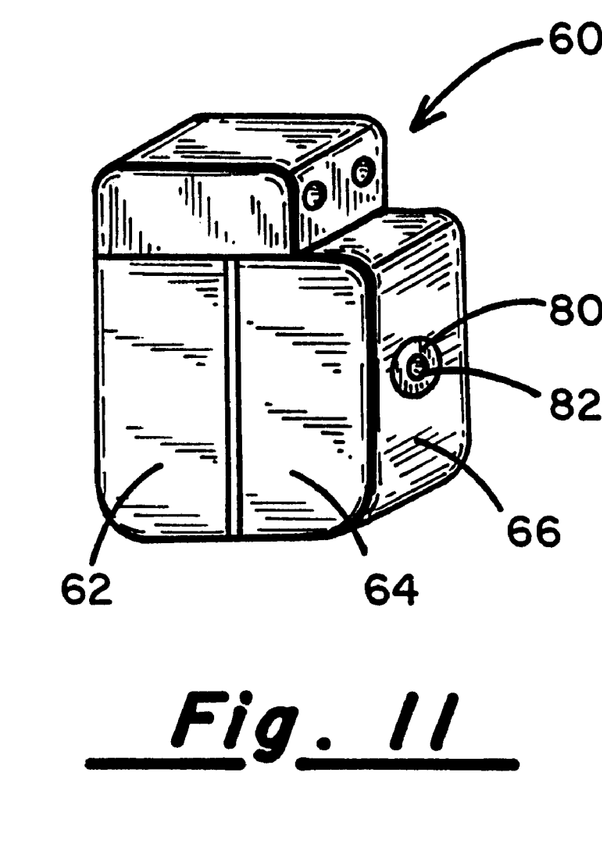
FIG. 11 is a perspective view of the pulse generator housing according to a sixth embodiment.

FIG. 11 illustrates a sixth embodiment in which regions of the conductive surface of the pulse generator housing are dedicated for certain functions. Specifically, the pulse generator housing 60 comprises electrically isolated conductive regions 62, 64 and 66. One or two of these regions may be dedicated for sensing purposes while others may be dedicated for shocking purposes. Each of these regions is connected to the pulse generator circuitry 18.

Additionally, a small isolated conductive surface 80 may be created by sputtering a small region of insulative material onto the body 52. A small region of conductive material such as platinum may be deposited onto the region 80. The region 82 is electrically connected to the pulse generator circuitry through the body 52.

Such a small conductive regional may serve as a return (ground) for a pacing configuration, sensing configuration, etc.

Figure 16:
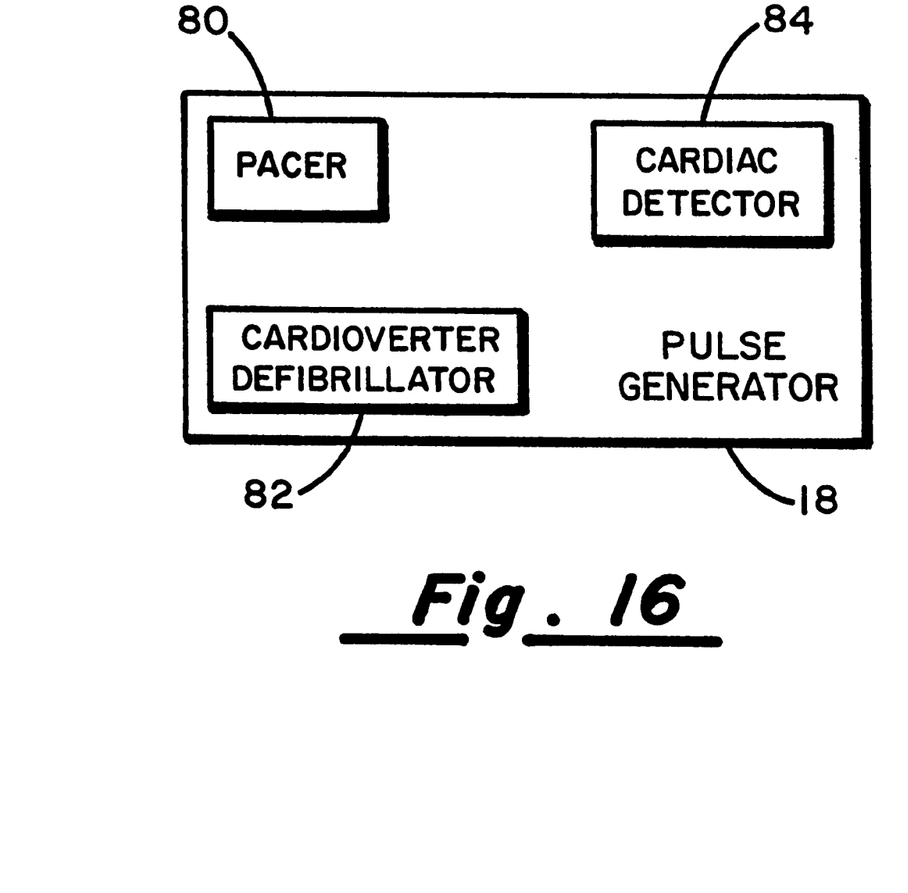
FIG. 16 is a block diagram illustrating the pulse generator.

Referring to FIG. 16, pulse generator circuitry 18 has full-function pacing capabilities (pacer 80) including pacing for bradycardia and tachyeardia both to inhibit an intrinsic beat or to adapt the rate to a higher or lower rate. In addition, circuitry 18 has cardioversion and defibrillation capabilities (cardioverter/defibrillator 82) and includes cardiac detection circuitry 84 capable of distinguishing when the heart is in normal sinus rhythm, should be paced, or requires higher energy cardioversion, or even higher energy defibrillation. The switch 16 is selectively activated to include or exclude the conductive surface of side wall 12 from the discharge sequence.

It is considered that the above description is intended by way of example only, and is not intended to limit the present invention in any way except as set forth in the following claims.

We claim:

1. An implantable heart treatment system having anti-arrhythmia pacemaking, cardioversion, and defibrillation capabilities for maintaining proper function of the heart, said system comprising:

an implantable pulse generator means for producing an anti-arrhythmia waveform;

a pulse generator housing enclosing and containing said pulse generator means, said pulse generator housing comprising an electrically conductive electrode removably attached to the housing and capable of electrical connection to said pulse generator;

an electrode for implantation in or about the heart and being electrically connected to said pulse generator for delivering electrical energy to the heart against said conductive surface of said pulse generator housing.

2. The implantable heart treatment system of claim 1, and further comprising sensor means for determining whether the pulse generator housing is inside a body of a patient or outside the body of a patient, said sensor means for disconnecting the conductive electrode of the pulse generator housing from the pulse generator means when the housing is outside the body of a patient.

3. An implantable heart treatment system having anti-arrhythmia pacemaking, cardioversion, and defibrillation capabilities for maintaining proper function of the heart, said system comprising:

an implantable pulse generator means for producing an anti-arrhythmia waveform;

a pulse generator housing enclosing and containing said pulse generator means, an electrically conductive electrode removably attached to said pulse generator housing and electrically connected to said pulse generator means;

a first electrode implanted in or about the heart and being electrically connected to said pulse generator;

a second electrode implanted in or about the heart and being electrically connected to said pulse generator;

switching means for directing said anti-arrhythmia waveform on the one hand, between at least one of said first and second electrodes and said conductive surface of said pulse generator housing upon a first condition of said heart, and on the other hand directing said anti-arrhythmia waveform to said first and second electrodes electrically connected in common against said conductive surface of said pulse generator housing upon a second condition of the heart.

4. An implantable heart treatment system for maintaining proper function of the heart, said system comprising:

an implantable pulse generator means for producing an anti-arrhythmia waveform;

a pulse generator housing enclosing and containing said pulse generator means and having a conductive portion, said conductive portion comprising an electrically conductive outer surface which is electrically connected to said pulse generator means and an electrically conductive electrode removably attached to said pulse generator housing and electrically connected to said pulse generator means;

a first heart electrode implanted in contact with the heart and being electrically connected to said pulse generator;

a second heart electrode implanted in contact with the heart and being electrically connected to said pulse generator;

switching means for directing said anti-arrhythmia waveform on the one hand, between at least one of said first and second heart electrodes and said conductive portion of said pulse generator housing upon a first condition of said heart, and on the other hand directing said anti-arrhythmia waveform to said first and second heart electrodes electrically connected in common against said conductive portion of said pulse generator housing upon a second condition of the heart.

* * * * *

UNITED STATES PATENT AND TRADEMARK OFFICE
CERTIFICATE OF CORRECTION

PATENT NO. : 5,916,238
DATED: June 29, 1999
INVENTOR(S) : Robert G. Hauser et al.

It is certified that error appears in the above-identified patent and that said Letters Patent is hereby corrected as shown below:

On the title page, under attorney, agent, or firm delete:
"Lundberg Woessner", and insert --Lundberg, Woessner--, therefore.

In column 1, line 7, delete "5,313" and insert --5,713-- so that the entire patent number is 5,713,926, therefore.

In column 1, line 12, delete "U.S. Pat. 5,133,353." and insert --U.S. Pat. No. 5,133,353.--, therefore.

In column 3, line 41, delete "programmabel" and insert --programmable--, therefore.

In column 7, line 3, delete "tachyeardia" and insert --tachycardia--, therefore.

Signed and Sealed this

Twenty-first Day of November, 2000

Attest:

Q. TODD DICKINSON

*Attesting Officer*     *Director of Patents and Trademarks*